United States Patent [19]

Böger et al.

[11] Patent Number: 4,555,405
[45] Date of Patent: Nov. 26, 1985

[54] CARBAMIC ACID ESTERS USEFUL AS PESTICIDES

[75] Inventors: Manfred Böger, Weil am Rhein, Fed. Rep. of Germany; Jozef Drabek, Oberwil, Switzerland

[73] Assignee: Ciba Geigy Corporation, Ardsley, N.Y.

[21] Appl. No.: 509,498

[22] Filed: Jun. 30, 1983

[30] Foreign Application Priority Data

Jul. 2, 1982 [CH] Switzerland .......................... 4054/82
Mar. 16, 1983 [CH] Switzerland .......................... 1437/83

[51] Int. Cl.⁴ ..................... A01N 47/10; A01N 37/34; C07C 121/66; C07C 125/04
[52] U.S. Cl. .............................. 514/488; 260/465 D; 560/17
[58] Field of Search ...................... 260/465 D; 560/17; 424/300, 304

[56] References Cited

U.S. PATENT DOCUMENTS 3,663,594  5/1972  Brown et al. ................ 424/300
3,929,838 12/1975  Siegle et al. ................. 560/17
4,486,449 12/1984  Kisida et al. ................ 424/300

*Primary Examiner*—Nicky Chan
*Attorney, Agent, or Firm*—Edward McC. Roberts

[57] ABSTRACT

Novel substituted N-alkyl-N-sulfenyl-carbamic acid-[2-(4-phenoxyphenoxy)- and 2-(4-phenylthiophenoxy)-ethyl] esters of the formula

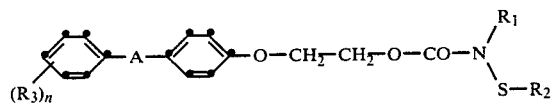

wherein
$R_1$ is $C_1$–$C_4$-alkyl, $R_2$ is phenyl, phenyl substituted by 1 or 2 halogen atoms or by 1 or 2 $C_1$–$C_4$-alkyl groups or is —$C(CH_3)_2$—C≡N, $R_3$ is halogen, $C_1$–$C_4$-alkyl, or $C_1$–$C_4$-alkyl substituted by up to 3 halogen atoms, A is oxygen or sulfur, and n is zero, 1 or 2; processes for producing this compound; and compositions for use in the control of pests, particularly the control of pests which infest plants and animals. The novel compounds are especially effective as ovicides against insects which damage plants.

19 Claims, No Drawings

CARBAMIC ACID ESTERS USEFUL AS PESTICIDES

The present invention relates to novel substituted N-alkyl-N-sulfenyl-carbamic acid-[2-(4-phenoxyphenoxy)- and 2-(4-phenylthiophenoxy)-ethyl]esters, to processes for producing them, and to their use for controlling pests.

The carbamic acid esters according to the invention have the formula I

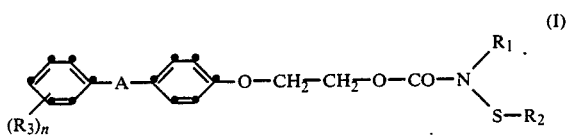

wherein
$R_1$ is $C_1$-$C_4$-alkyl,
$R_2$ is phenyl, phenyl substituted by 1 or 2 halogen atoms or by 1 or 2 $C_1$-$C_4$-alkyl groups, or is —$C(CH_3)_2$—$C\equiv N$,
$R_3$ is halogen, $C_1$-$C_4$-alkyl, or $C_1$-$C_4$-alkyl substituted by up to 3 halogen atoms,
A is oxygen or sulfur, and
n is zero, 1 or 2.

Preferred compounds of the formula I according to the invention are those wherein $R_2$ is phenyl, phenyl substituted by 1 or 2 fluorine, chlorine or bromine atoms or by 1 or 2 methyl groups, or is —$C(CH_3)_2$—$C\equiv N$, and $R_3$ is fluorine, chlorine, bromine, methyl or trifluoromethyl. Compounds of the formula I to be particularly emphasised are those wherein $R_2$ is phenyl, phenyl substituted by 1 or 2 chlorine atoms or methyl groups, or is —$C(CH_3)_2$—$C\equiv N$, and $R_3$ is chlorine or trifluoromethyl.

Further preferred compounds of the formula I are those wherein $R_3$ is in the 2- and/or 4-position on the phenyl ring, or those wherein $R_2$ is phenyl, 4-chlorophenyl, —$C(CH_3)_2$—$C\equiv N$ or 2,4-dimethylphenyl.

Of particular interest by virtue of their activity are also those compounds of the formula I wherein $R_3$ is 2—Cl, 4—Cl or 4—$CF_3$; those wherein $R_1$ is methyl or ethyl; and those wherein n is zero.

The compounds of the formula I can be produced by processes analogous to known processes (cp. for example European Patent Application No. 0,004,334 and British Patent Specification No. 1,573,620).

Thus, for example, a compound of the formula I can be obtained by reacting
(a) a compound of the formula II

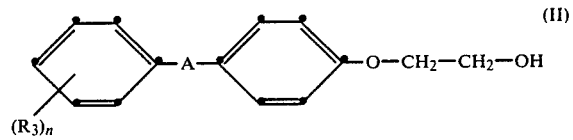

with a compound of the formula III

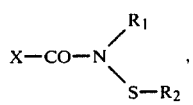

or
(b) a compound of the formula IV

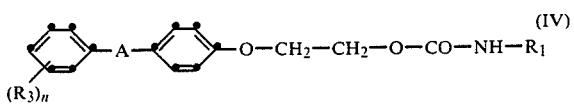

with a compound of the formula V

the symbols $R_1$, $R_2$, $R_3$, A and n in the formulae II to V having the meanings defined under the formula I in the foregoing, and X being halogen, preferably chlorine.

The stated processes (a) and (b) are preferably performed under normal pressure, and in the presence of an organic solvent or diluent. Suitable solvents or diluents are for example: ethers and ethereal compounds, such as dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; ketones, such as acetone, methyl ethyl ketone, methylisopropyl ketone and methylisobutyl ketone. The process (a) is generally performed at a temperature of $-10°$ to $200°$ C., preferably between $20°$ and $150°$ C., in particular at the boiling point of the employed inert solvent, and preferably in the presence of an acid acceptor. Process (b) is performed at a temperature of $-20°$ to $100°$ C., especially between $0°$ to $50°$ C., and preferably likewise in the presence of an acid acceptor. The acid acceptors employed in the said processes in the customary manner can be bases and basic substances. Preferred bases are tertiary amines, such as trialkylamines, for example triethylamine, pyridine, lutidines, and the like, which, when used in a stoichiometric excess, can simultaneously serve as solvent.

The starting materials of the formulae II to V are known, and can be produced by methods analogous to known methods.

N-Carboxy-carbamic acid phenyl esters having insecticidal and acaricidal properties are known from the German Offenlegungsschrift No. 2,132,936. Furthermore, substituted N-(4-phenoxyphenoxyethyl)- and N-(4-phenylthiophenoxyethyl)-carbamic acid alkyl esters are described, as development inhibitors having pesticidal activity, in the European Patent Application No. 0,004,334. And in addition, insecticidally and acaricidally effective, substituted N-alkyl-carbamic acid-(4-phenoxyphenoxyethyl)esters form subject matter of the British Patent Specification No. 1,573,620. On the other hand, in the case of the compounds according to the invention, they are novel substituted N-alkyl-N-sulfenyl-carbamic acid-(4-phenoxyphenoxyethyl)- and 4-phenylthiophenoxyethyl)-esters which, surprisingly, exhibit increased activity as pesticidal active substances.

A further advantage of the compounds of the formula I according to the invention is that they have negligible toxicity to warm-blooded animals and a high level of tolerance to plants.

The compounds of the formula I are particularly suitable for combating insects of the others: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. The compounds of the formula I also have an acaricidal action.

Besides having a favourable action against flies, for example *Musca domestica,* and against mosquito larvae, the compounds of the formula I can also be used for controlling insects which damage plants by eating, in crops of ornamental plants and productive plants, and also in fruit and vegetable crops (for example against *Laspeyresia pomonella, Leptinotarsa decemlineata,* Adoxophyes reticulana and *Epilachna varivestis*). The compounds of the formula I are distinguished in particular by a marked ovicidal action, especially against the eggs of insect pests which do damage by eating. When compounds of the formula I are taken up with the feed by adult insect stages, there is observed in many cases, especially with Coleoptera, for example Anthonomus grandis, a reduced oviposition and/or a lessened rate of hatching.

The compounds of the formula I can be used also for controlling ectoparasites, such as Lucilia sericata, and ectoparasitic acarids, in both domestic and productive animals, for example by treatment of animals, livestock housing and pasture land. The compounds according to the invention are particularly suitable for controlling zooparasitic ticks, such as Rhipicephalus bursa, Amblyomma helvaeum and Boophilus microplus.

The action of the compounds according to the invention, or of compositions containing them, can be considerably broadened and adapted to suit given circumstances by the addition of other pesticides. Suitable additives are for example the following active substances: organic phosphorus compounds, nitrophenols and derivatives thereof, formamidines, ureas, carbamates, chlorinated hydrocarbons, pyrethroids and Bacillus thuringienis preparations.

The compounds of the formula I can be combined with particular advantage also with substances which intensify pesticidal activity. Examples of compounds of this type are, inter alia: piperonylbutoxides, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The good insecticidal and acaricidal action of the compounds of the formula I according to the invention corresponds to a mortality rate of at least 50-60% of the pests mentioned.

The compounds of the formula I are used either in an unmodified form or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, and likewise the type of composition, are selected to suit the objectives to be achieved and the given conditions.

The formulations, that is to say, the compositions or preparations containing the active ingredient of the formula I, or combinations of this active ingredient with other insecticides or acaricides, and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalates, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as caclite, talcum, kaolin, montmorillonite or attapulgite. In order to improve the physical properties, it is also possible to add highly dispersed silicic acid or highly dispersed absorbent polymers.

Suitable granulated adsorptive carriers are porous types, for example pumice, ground brick, sepiolite or bentonite; and suitable nonsorbent carriers are materials such as calcite or sand. A great number of pregranulated materials of inorganic or organic nature, such as in particular dolomite or ground plant residues, can also be used.

Suitable surface-active compounds are, depending on the nature of the active substance of the formula I, or of the combinations of this active substance with other insecticides or acaricides, to be formulated, nonionic, cationic and/or anionic tensides having good emulsifying dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$-$C_{22}$), for example the sodium or potassium salts of oleic or stearic acid, or of natural fatty acid mixtures, which can be obtained for example from coconut oil or tallow oil. Also to be mentioned as tensides are the fatty acid-methyl-taurine salts, and also modified and unmodified phospholipides.

So-called synthetic tensides are however more frequently used, particularly fatty sulfonates, fatty sulfates, sulfonated benzimidazole derivatives or alkylarylsulfonates.

The fatty sulfonates or sulfates are as a rule in the form of alkali metal, alkaline-earth metal or unsubstituted or substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic tensides which may be mentioned are: nonylphenol-polyethoxyethanols, castor oil polyglycol ethers, polypropylene/polyethylene oxide adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyl-trimethyl ammonium chloride or benzyldi-(2-chloroethyl)-ethylammonium bromide.

The tensides customarily used in formulation practice are described, inter alia, in the following publications:

"Mc Cutcheon's Detergents and Emulsifiers Annual", MC Publishing Corp., Ringwood, N.J., 1981; H. Stache, "Tensid-Taschenbuch" (Tenside Manual), Carl Hauser Verlag, Munich/Vienna, 1981.

The pesticidal preparations contain as a rule 0.1 to 99%, particularly 0.1 to 95%, of active substance of the formula I, or of combinations of this active substance with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active substance.

The compositions can also contain additives such as stabilisers, antifoam agents, viscosity regulators, binders and adhesives, as well as fertilisers or other active substances for obtaining special effects.

Formulation examples for liquid active ingredients of the formula I or combinations of these active ingredients with other insecticides or acaricides (%=percent by weight)

| 1. Emulsion concentrates | (a) | (b) | (c) |
|---|---|---|---|
| active ingredient or active-ingredient combination | 25% | 40% | 50% |
| calcium dodecylbenzenesulfonate | 5% | 8% | 6% |
| castor-oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any concentration required can be produced from such concentrates by dilution with water.

| 2. Solutions | (a) | (b) | (c) | (d) |
|---|---|---|---|---|
| active ingredient or active-ingredient combination | 80% | 10% | 5% | 95% |
| ethylene glycol-monomethyl ether | 20% | — | — | — |
| polyethylene glycol MW 400 | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

The solutions are suitable for application in the form of very fine drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation examples for solid active ingredients of the formula I or combinations of these active ingredients with other insecticides or acaricides (%=percent by weight)

| 5. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient or the active ingredient combination is well mixed with the additives, and the mixture is thoroughly ground in a suitable mill. Wettable powders which can be diluted with water to give suspensions of the concentration required are obtained.

| 6. Emulsion concentrate | |
|---|---|
| active ingredient or active-ingredient combination | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |

| 6. Emulsion concentrate | |
|---|---|
| xylene mixture | 50% |

Emulsions of the concentration required can be obtained from this concentration by dilution with water.

| 7. Dusts | (a) | (b) |
|---|---|---|
| active ingredient or active-ingredient combination | 5% | 8% |
| talcum | 95% | — |
| kaolin | — | 92% |

Dusts ready for use are obtained by mixing the active ingredient with the carriers and grinding the mixture in a suitable mill.

| 8. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded, granulated, and subsequently dried in a stream of air.

| 9. Coated granules | |
|---|---|
| active ingredient or active-ingredient combination | 3% |
| polyethylene glycol (MW 200) | 3% |
| kaolin | 94% |

The finely ground active ingredient or the active-ingredient combination is evenly applied, in a mixer, to the kaolin moistened with polyethylene glycol. Dust-free coated granules are obtained in this manner.

| 10. Suspension concentrate | |
|---|---|
| active ingredient or active-ingredient combination | 40% |
| ethylene glycol | 10% |
| nonylphenol-polyethylene glycol (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a | 0.8% |

| 10. Suspension concentrate | |
|---|---|
| 75% aqueous emulsion | |
| water | 32% |

The finely ground active ingredient or the active-ingredient combination is intimately mixed with the additives. There is thus obtained a suspension concentrate from which can be prepared, by dilution with water, suspensions of the concentration required.

EXAMPLE 1

Production of N-methyl-N-(2-isobutyronitrile)-sulfenyl-carbamic acid-[2-(4-phenoxy)-phenoxyethyl]ester 9.2 g of 2-(4-phenoxy)-phenoxy-ethanol are stirred up at room temperature in 100 ml of toluene (anhydrous), 5 g of triethylamine and 0.4 g of 4-dimethylaminopyridine; and there are then slowly added dropwise 7.05 g of (2-fluorocarbonyl-4-cyano-4-methyl)-2-aza-3-sulfapentane dissolved in 20 ml of anhydrous toluene. The mixture is stirred at 100° for 10 hours; and water is then added to the resulting reaction mixture after cooling; the toluene phase is repeatedly washed with water, dried over sodium sulfate, and concentrated by evaporation. The yellow oil obtained is chromatographed through silica gel with dichloromethane. There is thus obtained, after concentration by evaporation, the title compound of the formula

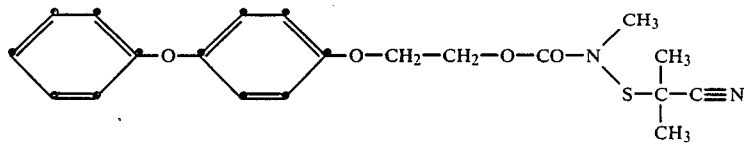

in the form of a light-coloured oil having a refractive index of $n_D^{20} = 1.5583$ (compound No. 1).

EXAMPLE 2

Production of N-ethyl-N-(4-chlorophenyl)-sulfenyl-carbamic acid-[2-(4-phenoxy)-phenoxyethyl]ester 9 g of N-ethyl-carbamic acid-[2-(4-phenoxy)-phenoxyethyl]ester are placed into 30 ml of pyridine, and, with stirring and cooling, 5.4 g of 4-chlorophenylsulfenyl chloride are slowly added dropwise at 5° to 10° C. The reaction mixture is subsequently stirred for 3 hours at 10° C. and then for 3 hours at room temperature; it is afterwards poured into a mixture of 300 ml of ice-water and 100 ml of toluene. The organic phase is washed with water, dried over sodium sulfate, and concentrated by evaporation. The resulting reddish oil is chromatographed through silica gel with a dichloromethane/hexane mixture (volume ratio 1:1), and finally with pure dichloromethane. There is thus obtained, after concentration by evaporation, the title compound of the formula

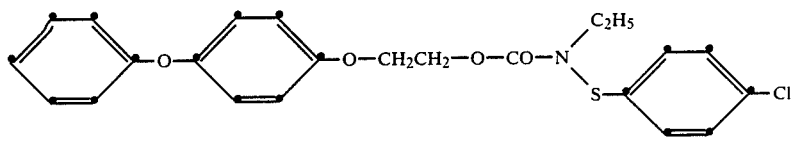

as colourless oil having the refractive index of $n_D^{20}=1.5949$ (compound No. 2).

The following compounds of the formula I were produced by a procedure analogous to that described in the foregoing:

| Compound No. | $R_3$ | n | A | $R_1$ | $R_2$ | Physical data |
|---|---|---|---|---|---|---|
| 3 | — | 0 | —O— | —$C_2H_5$ | —$C(CH_3)_2CN$ | $n_D^{20} = 1.5520$ |
| 4 | — | 0 | —O— | —$C_2H_5$ | 2,6-(CH₃)₂-phenyl | $n_D^{20} = 1.5864$ |
| 5 | 4-$CF_3$ | 1 | —O— | —$C_2H_5$ | phenyl | $n_D^{20} = 1.5609$ |
| 6 | 2-Cl, 4-Cl | 2 | —O— | —$C_2H_5$ | phenyl | $n_D^{20} = 1.6038$ |
| 7 | 2-Cl, 4-$CF_3$ | 2 | —O— | —$C_2H_5$ | phenyl | $n_D^{20} = 1.5721$ |
| 8 | — | 0 | —O— | n-$C_3H_7$ | phenyl | $n_D^{20} = 1.5900$ |
| 9 | — | 0 | —O— | n-$C_4H_9$ | phenyl | $n_D^{20} = 1.5850$ |
| 10 | — | 0 | —O— | n-$C_4H_9$ | 4-Cl-phenyl | $n_D^{20} = 1.5860$ |
| 11 | — | 0 | —S— | —$C_2H_5$ | phenyl | $n_D^{25} = 1.6180$ |
| 12 | — | 0 | —S— | —$C_2H_5$ | 4-Cl-phenyl | $n_D^{25} = 1.6192$ |
| 13 | — | 0 | —S— | —$C_2H_5$ | —$C(CH_3)_2CN$ | $n_D^{25} = 1.5769$ |
| 14 | — | 0 | —O— | n-$C_3H_7$ | —$C(CH_3)_2CN$ | $n_D^{22} = 1.5469$ |
| 15 | — | 0 | —O— | n-$C_4H_9$ | —$C(CH_3)_2CN$ | $n_D^{22} = 1.5412$ |
| 16 | 4-Cl | 1 | —O— | —$CH_3$ | —$C(CH_3)_2CN$ | $n_D^{20} = 1.5626$ |
| 17 | 4-Cl | 1 | —S— | —$C_2H_5$ | —$C(CH_3)_2CN$ | $n_D^{20} = 1.5819$ |

The following compounds of the formula I are obtainable in a corresponding manner:

| Comp. No. | $R_3$ | n | A | $R_1$ | $R_2$ |
|---|---|---|---|---|---|
| 18 | 4-F | 1 | —O— | —$C_2H_5$ | 4-Cl-phenyl |
| 19 | — | 0 | —O— | —$C_2H_5$ | 4-$C(CH_3)_3$-phenyl |
| 20 | 4-$CH_3$ | 1 | —O— | —$C_2H_5$ | —$C(CH_3)_2CN$ |
| 21 | — | 0 | —O— | —$CH_3$ | 2,6-(CH₃)₂-phenyl |
| 22 | — | 0 | —O— | —$C_2H_5$ | 2,3-Cl₂-phenyl |
| 23 | — | 0 | —O— | —$CH_3$ | 4-$C(CH_3)_3$-phenyl |

-continued

| Comp. No. | R₃ | n | A | R₁ | R₂ |
|---|---|---|---|---|---|
| 24 | 4-C(CH₃)₃ | 1 | —O— | —C₂H₅ | —C(CH₃)₂CN |

EXAMPLE 3

Action against *Musca domestica*

50 g of freshly prepared CSMA nutrient medium for maggots are weighed off into each of a series of beakers. A specific amount of a 1% (by weight) acetonic solution of the respective active substance is transferred by pipette to the nutrient medium in each beaker so that active-substance concentrations of 0.1–0.01% are obtained. After a thorough mixing of the nutrient medium, the acetone is allowed to evaporate off for at least 20 hours.

There are then deposited per active substance and concentration in each case 25 one-day-old Musca domestica maggots into each beaker containing the treated nutrient medium. After completion of pupation, the formed pupae are separated from the nutrient medium by flushing with water, and are placed into vessels closed with perforated lids.

The pupae flushed out per batch are counted (toxic effect of the active substance on the development of the maggots), and after 10 days the number of flies which have emerged from the pupae is determined.

Compounds of the formula I according to the Examples 1 and 2 in the foregoing exhibit a good action in the above test.

EXAMPLE 4

Action against *Lucilia sericata*

1 ml of an aqueous preparation containing 0.5% of active substance is added to 9 ml of a culture medium at 50° C. About 30 freshly hatched Lucilia sericata maggots are then placed onto the culture medium, and after 48 and 96 hours, respectively, the insecticidal action is determined by ascertaining the mortality rate.

Compounds of the formula I according to Examples 1 and 2 exhibit in this test a good action against Lucilia sericata.

EXAMPLE 5

Action against *Aedes aegypti*

Sufficient of a 0.1% acetonic solution of the respective active substance is transferred by pipette to the surface of 150 ml of water in a container to obtain concentrations of 800 and 400 ppm in each case. After the acetone has evaporated off, 30–40 two-day-old Aëdes larvae are placed into each container. The mortality rate is ascertained after 1, 2 and 5 days.

Compounds of the formula I according to the Examples 1 and 2 in the foregoing exhibit in this test a good action against Aëdes aegypti.

EXAMPLE 6

Insecticidal stomach-poison action

Potted cotton plants about 25 cm in height are sprayed with aqueous active-substance emulsions containing the active substance at concentrations of 400 and 800 ppm, respectively. After the drying of the applied coating, larvae of Spodoptera littoralis in the $L_3$-stage, and of Heliothis virescens in the $L_3$-stage, respectively, are settled onto the cotton plants. The test is carried out at 24° C. with 60% relative humidity. The % mortality rate of the test insects is determined after 120 hours.

Compounds of the formula I according to Examples 1 and 2 in the foregoing exhibit a good action in this test.

EXAMPLE 7

Action against *Epilachna varivestis*

Phaseolus vulgaris plants (bush beans) about 15–20 cm in height are sprayed with aqueous emulsion preparations containing the active substance to be tested at concentrations of 400 ppm and 800 ppm, respectively. After the drying of the applied coating, 5 larvae of Epilachna varivestis (Mexican bean beetle) in the 4th larval stage are settled onto each plant. A plastics cylinder covered with a copper-gauze lid is placed over each treated plant. The test is carried out at 28° C. with 60% relative humidity. After 2 and 3 days, respectively, the acute action (% mortality) is determined. The test insects are observed for a further 3 days to effect an evaluation with respect to any damage to the plants from eating (antifeeding effect), and disturbances in development and in shedding.

Compounds of the formula I according to Examples 1 and 2 in the foregoing exhibit a good action in the above test.

EXAMPLE 8

Ovicidal action against *Heliothis virescens*

Corresponding proportions of a wettable pulverulent formulation containing 25% by weight of the active substance to be tested are mixed with specific amounts of water to give aqueous emulsions of increasing concentration of active substance.

One-day-old clusters of eggs of Heliothis deposited on cellophane are immersed for three minutes in the above respective emulsions containing the active substance to be tested, and are then filtered by suction on round filters. The egg clusters treated in this manner are subsequently laid out in Petri dishes and kept in darkness. After 6 to 8 days, the hatching rate compared with that of untreated control clusters is determined. The basis for the evaluation is the minimum concentration of active substance required to effect a 100% kill of the eggs.

Compounds of the formula I according to Examples 1 and 2 in the foregoing exhibit a good action in the above test.

EXAMPLE 9

Action against *Laspeyresia pomonella* (eggs)

Deposited Laspeyresia pomonella eggs, not more than 24 hours old, are immersed on filter paper for 1 minute in acetonic/aqueous solutions containing increasing amounts of the active substance to be tested. After the drying of the solution on the eggs, these are laid out in Petri dishes and kept at a temperature of 28° C. The percentage hatching rate from the treated eggs is evaluated after six days.

The compound No. 1 according to Example 1 exhibits a 100% action (mortality) in the above test at an active-substance concentration of 0.2 ppm; and at an active-substance concentration of 0.02 ppm, the compounds Nos. 3, 4, 12 and 13 exhibit an 80–100% action. An 80–100% action is exhibited by the compounds Nos. 11 and 14 at 0.75 ppm; the compound No. 8 at 3 ppm;

the compound No. 2 at 50 ppm; the compounds Nos. 6 and 15 at 100 ppm; the compounds Nos. 5 and 9 at 200 ppm; and the compounds Nos. 7 and 10 at 400 ppm.

EXAMPLE 10

Effect on reproduction of *Anthonomus grandis*

Adult Anthonomus grandis, which have been hatched no longer than 24 hours, are transferred, in groups each of 25 beetles, to cages having lattice walls. The cages containing the beetles are then immersed for 5 to 10 seconds in an acetonic solution containing 1.0% by weight of the active substance to be tested.

After the beetles are again dry, they are placed, for copulation and oviposition, into covered dishes containing feed. Deposited eggs are flushed out with running water two to three times weekly; they are counted, disinfected by being placed for two to three hours into an aqueous disinfectant, and then deposited into dishes containing a suitable larval diet. An examination is made after 7 days to determine whether larvae have developed from the deposited eggs.

In order to ascertain the duration of the reproduction-influencing effect of the active substances tested, the oviposition of the beetles is observed during a period of about four weeks. The evaluation is on the basis of the reduction in the number of eggs laid and larvae hatched in comparison with that in the case of untreated control specimens.

Compounds of the formula I according to Examples 1 and 2 in the foregoing exhibit a good reproduction-influencing effect in the above test.

EXAMPLE 11

Test of action against ticks: killing effect in various stages of development

The test specimens used are larvae (in each case about 50), nymphs (in each case about 25) and imagines (in each case about 10) of the tick species Rhipicephalus bursa, Amblyomma hebraeum and Boophilus microplus. The test insects are immersed for a short time in aqueous emulsions or solutions of the substances to be tested at specific concentrations. The emulsions or solutions contained in small test tubes are then absorbed onto cotton wool, and the wetted test insects are left in the treated test tubes. An evaluation is made for larvae after 3 days and for nymphs and imagines after 14 days.

There is determined the minimum substance concentration which effects a 100% mortality rate, expressed in ppm of active substance, relative to the total amount of emulsion or solution.

The compounds of the formula I according to Examples 1 and 2 are effective in the following concentration ranges:
  larvae: <0.1–100 ppm
  nymphs: <1–10 ppm
  adults: <10–500 ppm.

What is claimed is:

1. A compound of the formula

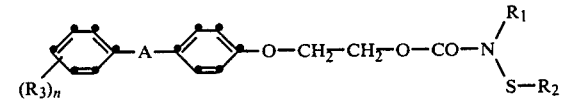

wherein
  $R_1$ is $C_1$–$C_4$-alkyl,
  $R_2$ is phenyl, phenyl substituted by 1 or 2 halogen atoms or 1 or 2 $C_1$–$C_4$-alkyl groups, or is —$C(CH_3)_2$—C≡N,
  $R_3$ is halogen, $C_1$–$C_4$-alkyl, or $C_1$–$C_4$-alkyl substituted by up to 3 halogen atoms,
  A is oxygen or sulfur, and
  n is zero, 1 or 2.

2. A compound according to claim 1, wherein $R_3$ is substituted in the 2- and/or 4-position on the phenyl ring.

3. A compound according to claim 1, wherein $R_2$ is phenyl, phenyl substituted by 1 or 2 fluorine, chlorine or bromine atoms or by 1 or 2 methyl groups, or is —$C(CH_3)_2$—C≡N, and $R_3$ is fluorine, chlorine, bromine, methyl or trifluoromethyl.

4. A compound according to claim 2, wherein $R_2$ is phenyl, phenyl substituted by 1 or 2 chlorine atoms or methyl groups, or is —$C(CH_3)_2$—C≡N, and $R_3$ is chlorine or trifluoromethyl.

5. A compound according to claim 4, wherein $R_2$ is phenyl, 4-chlorophenyl, 2,4-dimethylphenyl or —$C(CH_3)_2$—C≡N.

6. A compound according to claim 1, wherein $R_3$ is 2—Cl, 4—Cl or 4—$CF_3$.

7. A compound according to claim 1, wherein $R_1$ is methyl or ethyl.

8. A compound according to claim 1, wherein n is zero.

9. A compound according to claim 8 of the formula

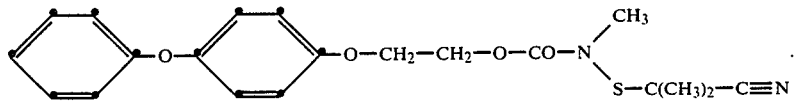

10. A compound according to claim 8 of the formula

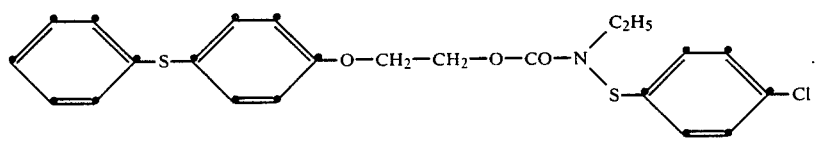

11. A compound according to claim 8 of the formula

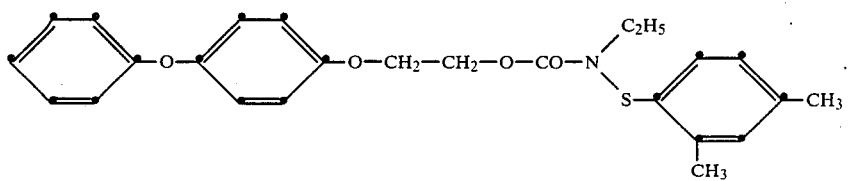

12. A compound according to claim 8 of the formula

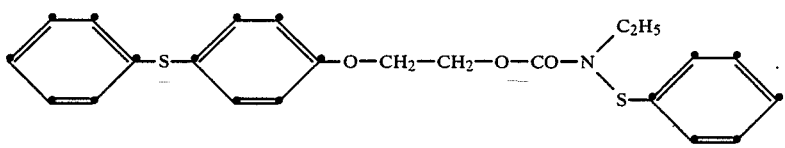

13. A compound according to claim 8 of the formula

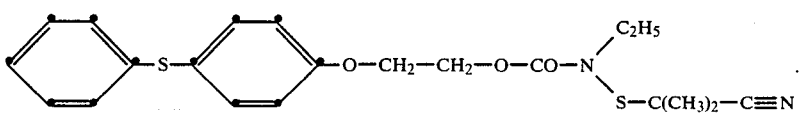

14. A compound according to claim 8 of the formula

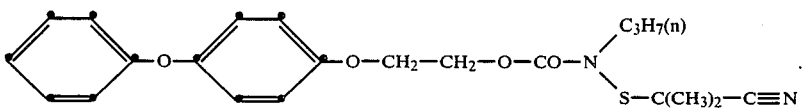

15. A pesticidal composition for the control of insects and acarids which contains as active ingredient a pesticidally effective amount of a compound according to claim 1, together with a suitable carrier and/or other additives.

16. A method of controlling pests, selected from the group consisting of insects, and members of the order Acarina, which method comprises applying thereto or to the locus thereof a pesticidally effective amount of a compound according to claim 1.

17. A method according to claim 16 wherein the pests are insects which damage plants.

18. A method according to claim 17, which method comprises applying the compound as an ovicide.

19. A method of claim 16 wherein the pests are insects.

* * * * *